(12) United States Patent
Ralph et al.

(10) Patent No.: US 8,915,921 B2
(45) Date of Patent: Dec. 23, 2014

(54) AUTOLOGOUS BONE HARVEST DURING OSTEOTOMY AND BONE DRILLING PROCEDURES

(75) Inventors: James D. Ralph, Bethlehem, PA (US); Thomas N. Troxell, Pottstown, PA (US); Mark Michels, Glen Mills, PA (US)

(73) Assignee: BioDynamics LLC, Englewood, NJ (US)

( * ) Notice: Subject to any disclaimer, the term of this patent is extended or adjusted under 35 U.S.C. 154(b) by 0 days.

(21) Appl. No.: 12/823,427

(22) Filed: Jun. 25, 2010

(65) Prior Publication Data

US 2010/0298835 A1   Nov. 25, 2010

Related U.S. Application Data

(63) Continuation of application No. 11/409,816, filed on Apr. 24, 2006, now abandoned.

(51) Int. Cl.
| | | |
|---|---|---|
| *A61B 17/00* | (2006.01) | |
| *A61B 17/16* | (2006.01) | |
| *A61B 17/17* | (2006.01) | |
| *A61F 2/46* | (2006.01) | |

(52) U.S. Cl.
CPC .............. *A61B 17/1635* (2013.01); *A61B 17/17* (2013.01); *A61F 2/4644* (2013.01); *A61B 17/1695* (2013.01); *A61B 17/1728* (2013.01); *A61B 2017/00969* (2013.01); *A61B 2217/005* (2013.01); *A61B 2217/007* (2013.01); *A61F 2002/4645* (2013.01); *A61B 17/1739* (2013.01); *Y10S 606/903* (2013.01)
USPC ............................................ 606/80; 606/903

(58) Field of Classification Search
USPC .................. 606/79–85, 87, 96, 86 R; 408/67; 241/169.2
See application file for complete search history.

(56) References Cited

U.S. PATENT DOCUMENTS

| | | | | |
|---|---|---|---|---|
| 3,936,213 A | * | 2/1976 | Kappel ............................ | 408/67 |
| 4,111,208 A | * | 9/1978 | Leuenberger ................... | 606/80 |
| 4,705,500 A | | 11/1987 | Reimels et al. | |
| 4,765,333 A | | 8/1988 | Bray | |

(Continued)

FOREIGN PATENT DOCUMENTS

| | | |
|---|---|---|
| SU | 762870 A | 9/1980 |
| SU | 929081 A | 5/1982 |

(Continued)

OTHER PUBLICATIONS

First Official Action from Patent Office in Russian counterpart application in Russian language with English language translation.

(Continued)

*Primary Examiner* — Matthew Lawson
(74) *Attorney, Agent, or Firm* — Lowenstein Sandler LLP

(57) ABSTRACT

An apparatus and method for collecting particulate bone from the operating site during an osteotomy or bone drilling procedure so that it can be used subsequently to augment the bone fusion process. A bone cutting or drilling tool is provided with a module for collecting particulate bone simultaneously with cutting or drilling the bone. The collected particulate bone is transferred continuously to a sterile containment module and maintained under sterile conditions until it is prepared for re-use in the patient.

6 Claims, 16 Drawing Sheets

(56) References Cited

U.S. PATENT DOCUMENTS

| | | | |
|---|---|---|---|
| 4,844,064 A | 7/1989 | Thimsen et al. | |
| 5,304,191 A * | 4/1994 | Gosselin | 606/172 |
| 5,569,254 A | 10/1996 | Carlson et al. | |
| 5,913,859 A * | 6/1999 | Shapira | 606/80 |
| 6,022,354 A * | 2/2000 | Mercuri et al. | 606/80 |
| 6,325,806 B1 | 12/2001 | Fox | |
| 6,332,886 B1 | 12/2001 | Green et al. | |
| 6,358,252 B1 * | 3/2002 | Shapira | 606/80 |
| 6,506,199 B2 * | 1/2003 | Rogers et al. | 606/172 |
| 6,514,258 B1 | 2/2003 | Brown et al. | |
| 6,783,532 B2 | 8/2004 | Steiner et al. | |
| 6,783,533 B2 | 8/2004 | Green et al. | |
| 6,846,314 B2 | 1/2005 | Shapira | |
| 7,033,359 B2 * | 4/2006 | Meller | 606/80 |
| 7,077,845 B2 | 7/2006 | Hacker et al. | |
| 2003/0078586 A1 * | 4/2003 | Shapira | 606/80 |
| 2004/0049128 A1 | 3/2004 | Miller et al. | |
| 2004/0210229 A1 | 10/2004 | Meller | |
| 2006/0173426 A1 | 8/2006 | Urich et al. | |
| 2006/0229624 A1 | 10/2006 | May et al. | |
| 2007/0225665 A1 | 9/2007 | Perez-Cruet et al. | |

FOREIGN PATENT DOCUMENTS

| | | |
|---|---|---|
| SU | 1465033 A1 | 3/1989 |
| SU | 1565644 A1 | 5/1990 |
| WO | 05/56224 | 6/2005 |
| WO | 00/45712 | 8/2010 |

OTHER PUBLICATIONS

International Search Report dated Mar. 24, 2008.
European Search Report dated May 15, 2009.
European Search Report dated Feb. 13, 2007.

* cited by examiner

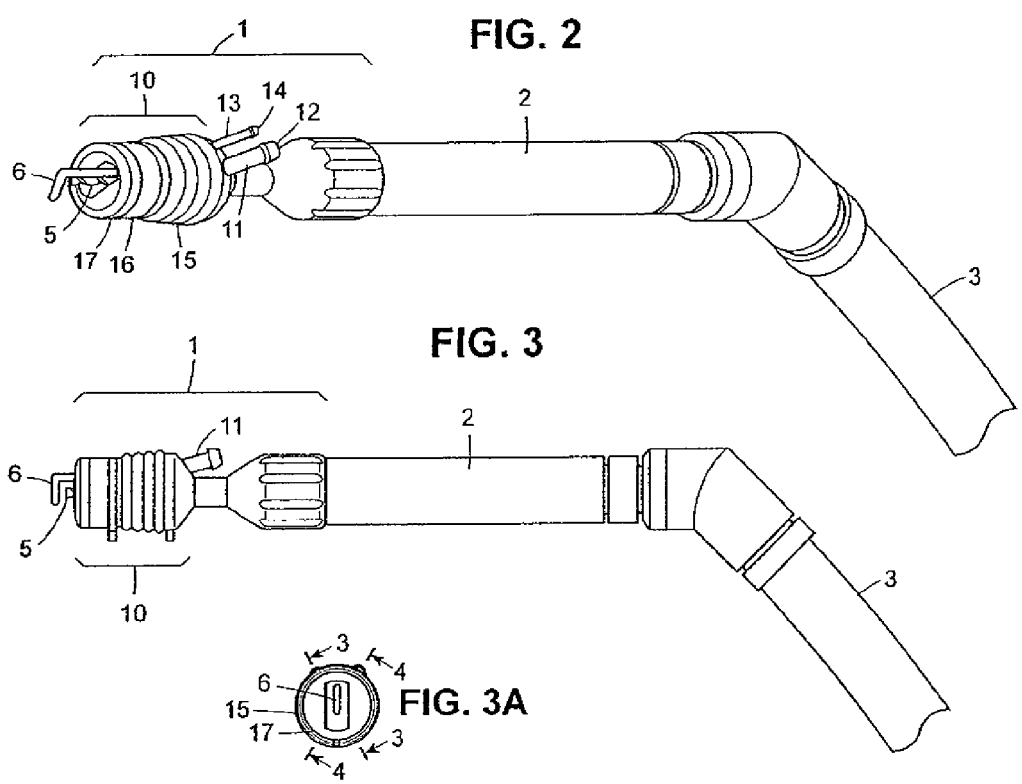

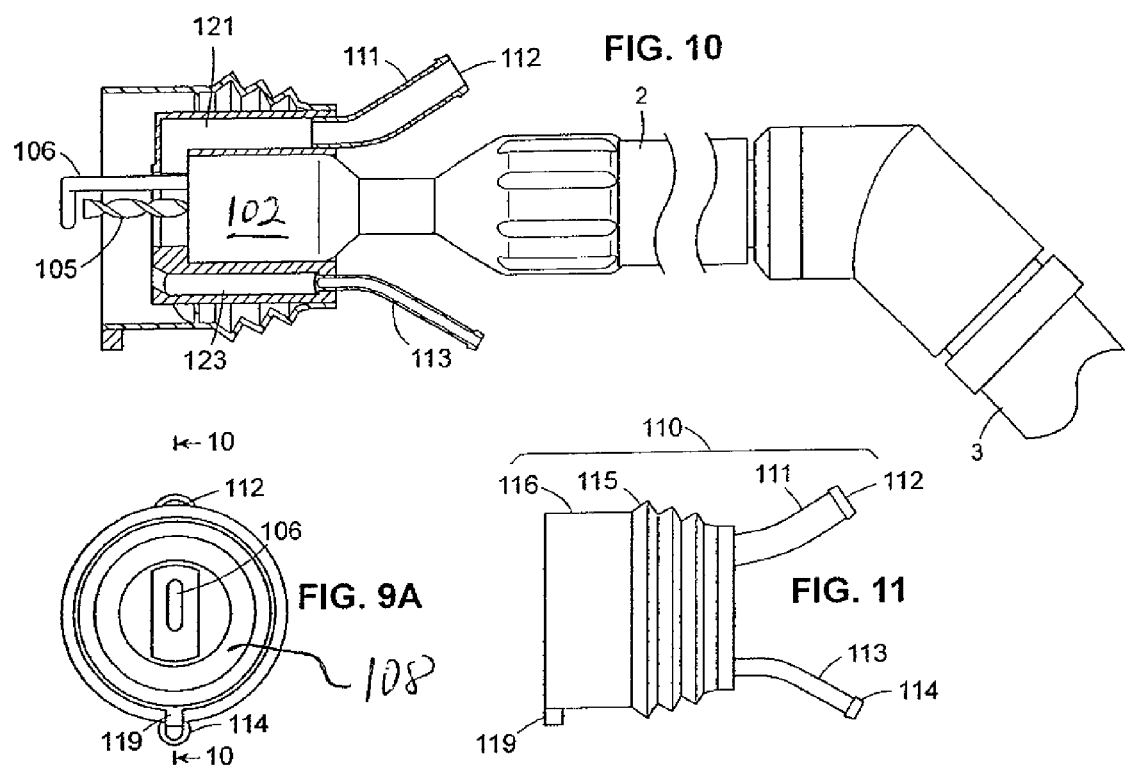

AUTOLOGOUS BONE HARVEST DURING OSTEOTOMY AND BONE DRILLING PROCEDURES

CROSS-REFERENCE TO RELATED APPLICATION

This application is a continuation of Ser. No. 11/409,816 filed Apr. 24, 2006 now abandoned.

BACKGROUND OF THE INVENTION

1. Field of the Invention

The present invention has to do with apparatus and methods for performing osteotomies and drilling holes in bones. More specifically, the invention relates to apparatus and methods for harvesting bone from the operating site during the osteotomy or bone drilling procedure so that it can be used to augment the bone fusion process.

2. The Related Art

Osteotomies are routinely performed for surgical access or to divide (and reposition) a bone for the correction of a skeletal deformity. Holes may be drilled in bones for various reasons to accommodate screws, pins and various other implantable devices and materials or to take a bone sample for analysis.

One of the more common examples of an osteotomy for surgical access is a craniotomy. In this procedure, the surgeon removes a significant portion of the patient's skull (termed a craniotomy flap, a cranial flap, a skull flap or bone flap) for access to the brain. The removed section of the skull is set aside in a sterile field and at the end of surgery, it is returned to its original position and affixed to the native skull, typically with plates and screws. The intent of the surgeon is to restore the patient's skull to its original contour and to provide physical protection for the brain. The ideal outcome would be complete fusion of the craniotomy flap to the native skull, leaving no long term bony deficit or weakness. In addition, many surgeons would prefer there to be minimal foreign bodies remaining and no imaging artifacts postoperatively. Unfortunately this is difficult to accomplish with the current surgical techniques.

The surgical instrument used to cut the craniotomy (a craniotome) utilizes a rotating cutter approximately 2 mm in diameter. The bone that is removed by this instrument is lost during surgery and as a result, when the cranial flap is returned to its original position, there is a gap around the entire periphery which corresponds to the diameter of the cutter. This gap creates a number of problems. The most obvious deficiency is that bone-to-bone contact, essential for achieving bony fusion, is impossible around the periphery of the cranial flap. This continuous gap (or kerf) creates a surgical "dead space" which is never desirable, it also allows soft tissue (the scalp and dura) to intrude into this space and inhibit bony healing. The step-off between the skull and cranial flap also may result in a cosmetic deformity for the patient. To combat these problems, surgeons use one or more strategies which have their own shortcomings. For example, the surgeon may choose to bias the cranial flap toward one side of the craniotomy. This produces bone-to-bone contact in a local area but increases the gap elsewhere around the periphery.

The surgeon may also elect to fill the gap between the skull and skull flap with a material which will encourage bony fusion. These fill materials can be autologous, allograft, or artificial. Autologous bone grafts are harvested directly from the patient and are the "gold standard," since they are inherently biocompatible, osteoconductive, osteoinductive, and osteogenic. Harvesting autologous bone is currently carried out by taking bone from a part of the patient's body other than the surgical site. This results in additional surgical time and the additional (surgical) harvest has its own attendant risk of complications such as donor site pain and morbidity. Allografts, derived from donor (cadaver) tissues, are only osteoconductive, and they involve considerable cost, pose the risk of disease transmission and are objectionable to certain religious groups. Artificial materials such as alloplastic bone cement are another alternative. These bone cements are almost always used in conjunction with plates and screws. The drawbacks to this approach include substantial additional cost, risk of infection and no certainty that the bone cement will ever remodel into actual bone.

While this problem is illustrated with a craniotomy example, it occurs whenever an osteotomy is created strictly for surgical access and the bones must be returned to their original positions in order to prevent a postoperative deformity or a functional problem. In the skull alone, this problem exists in skull base surgery, craniofacial tumor surgery and mandibular osteotomies for oncologic resection. At the conclusion of all these procedures, the surgical goal is to restore the original bony anatomy. This precludes achieving bone-to-bone contact of the severed ends since they must remain separated by the width of the blade (or cutter) used for the osteotomy.

Perforations (or holes) are routinely created in bones for surgical access and other reasons. These perforations may be performed for biopsy purposes, to create access for minimally invasive surgery or as the prelude to an osteotomy. An example of the latter is the burr hole that is initially created in the skull which allows the craniotome to be inserted for completion of the craniotomy. In these cases, it is desirable to close the perforation, preferably in a manner which restores the bone to its original condition. Additionally, holes are routinely drilled into bone as a step in preparation for orthopedic screw or pin insertion. Most of these cases would also benefit from the availability of autologous bone graft.

When osteotomies are used to divide a bone so that it may be repositioned to correct a surgical deformity, a different problem exists. In many cases, bone graft material is needed to fill the gaps created as the bones are repositioned and severed bony ends move relative to each other. This is obviously the case where a gap is intentionally created, such as an osteotomy to elevate a collapsed tibial plateau. It also may occur when the intent of the osteotomy is to decrease the bone volume. In these surgeries it is not uncommon for the contours of the bony ends to be slightly mismatched and in these cases the surgeon may elect to augment the fusion with additional bone graft material. As previously discussed, allograft bone, autogenous bone or alloplastic materials may all be used in such situations, each with their related problems.

In all these procedures where an osteotomy (or perforation) is necessary, a common problem exists: bone is removed by the osteotomy or drilling instrument and at the conclusion of surgery, additional bone is required to complete the reconstruction.

The current surgical practice is to manually irrigate the bone as it is cut and also to manually suction off the resulting solids and liquids into the operating room's non-sterile vacuum system. These activities are performed concurrently by other operating room personnel while the surgeon operates the osteotomy instrument. Some of the shortcomings of these practices are detailed in the following text which is excerpted from the USC Neurosurgery website. (http://uscneurosurgery.com/infonet/ecrani/instruments.htm).

Irrigation

With even optimal illumination and magnification and organization of his field, the surgeon is still incapacitated by obscuring blood, cloudy irrigation fluid, or other debris. Efficient intracranial surgery requires keeping the operative field clear of physical and visual obstacles by diligent irrigation, attentive aspiration, and meticulous hemostasis.

Irrigation and aspiration are complimentary aspects of surgical field maintenance. The irrigating-aspirating assistant must concentrate on following the movements of the surgeon's hands visually and with irrigant and suction. Areas of surgical interest are most safely addressed at the time of maximal cleanliness; immediately after they have been washed clean and aspirated dry.

Irrigant should be squirted onto the field under enough pressure to displace blood, but if the bulb is squeezed too hard and fluid issues under too much pressure, fluid from the bulb will be reflected back against the stream because it cannot dissipate fast enough, with the consequence that a splashing of mixed blood-irrigant fluid ends up in the surgeon's face and widely scattered across the field. Better control of the stream from the irrigation fluid bulb is achieved by manipulating it with the dominant hand.

The primarily aqueous solution used for surgical irrigation not only dilutes the blood but pushes it ahead of the irrigant stream. This washing force is greatest at the tip of a irrigation bulb where the irrigant fluid pressure is maximal.

Suction

Blood accumulates with irrigation fluid in dependent portions of the field as it escapes and is washed from lacerated vessels. The bloody fluid then interferes with the working of the electrocautery devices used to stop further bleeding from the openings in the vessels. To this is added the problem of blood's opacity, so that even in small quantities as even a thin layer, it obscures the surgical field.

Suction is a maintenance activity, keeping the operative field clear of debris, blood, or smoke that can obstruct visualization. Whenever possible the suction attachment should be held in the non-dominant hand.

Surgical field suction instrumentation attaches to the same suction canisters which provide suction for anesthesia. Distally non-sterile, proximally sterile tubing connects the suction device to the distal end of the metal suction handle and tip. The proximal end of the metal sucker connects to the suction tubing.

The importance and difficulty of performing simultaneous irrigation and suction in concert with the surgeon's movements are detailed above. Later in the text they discuss the importance of irrigation when cutting the bone:

Bone is perforated and/or cut in the course of any intracranial trauma surgery. Irrigation accomplishes two purposes in the setting of drilling bone. First, it cools down the bone. This is important in terms of the mechanics of bone cutting. The bits cut more effectively through cooler bone and in the absence of bone dust that can clog its rotations.

These comments are directed toward neurosurgical craniotomies but the same principles apply to all osteotomies and perforations. Proper irrigation not only improves the efficiency of the cutting instrument, it also prevents thermal necrosis of the bone which can later retard the healing process. This principle takes on even greater importance when one intends to collect the bone particles generated during the cutting process and reuse them in surgery. Irrigation has traditionally been conducted using a liquid. But according to the present invention we can irrigate with a liquid or compressed gas source or a combination of liquid and a compressed gas source. The compressed gas can be chilled if required and also can be intermixed with a fluid (e.g., saline).

Up until now, a reliable and essentially free source of autogenous bone has been overlooked by the surgical community. Manufacturers of surgical cutting instruments have incorporated irrigation on some instruments but none have ever proposed taking the concept one step further—collecting the bone particulate in a sterile fashion for later use in the bony reconstructive phase of the surgery.

We have now developed apparatus and methods for sterilely collecting and containing the particulate bone created during osteotomy and bone drilling procedures. The apparatus and methods also enable more controlled irrigation of the bone as it is cut or drilled and a reduction in the amount of patient bone that is scattered or aerosolized during surgery.

The terms particulate bone, bone particulate and bone particles are used interchangeably in this patent and all are intended to have the same meaning.

SUMMARY OF THE INVENTION

A collection module is provided on the cutting end, also referred to herein as the distal end, of a bone cutting tool to prevent the scatter and loss of particulate bone created at the operating site during an osteotomy or bone drilling procedure. The collection module suctions off the bone particulate as well as irrigant, blood and other body fluids and reduces contamination of the surgical field from the cutting operation. The module can be partially or completely disposable.

The collection module contains a suction port which evacuates the particulate bone from the cutting operation. A sterile containment module is provided downstream for collecting the particulate bone and separating it from irrigant and body fluids suctioned off from the surgical field.

An irrigation system is incorporated in some cutting tools and when it is not, it can be incorporated in the collection module to provide a reliable and effective source of irrigation to the cutting area. The irrigant prevents thermal necrosis, prevents the formation of bone dust, improves cutting efficiency and improves visibility within the surgical field. As previously disclosed, the irrigation system in our invention can disperse fluids, gasses or a combination of the two.

The sterile bone particles which are harvested according to the invention are used to augment the reconstructive portion of the surgery. The particulate bone can be used "as is" or mixed with any number of readily available additives such as, but not limited to:

a. Patient's blood;
  b. Patient's platelet rich plasma (PRP);
  c. Bone morphogenic proteins;
  d. Other bone growth factors; and
  e. Antibiotics.

BRIEF DESCRIPTION OF THE DRAWINGS

The drawing figures are provided for purposes of illustrating the elements of the invention and are not intended to be drawn to scale.

FIG. 2 is a perspective view of the craniotome of FIG. 1 with the collection module and the pneumatic line attached.

FIG. 3 is an elevation view of the craniotome of FIG. 2.

FIG. 3A is a view of the left end of FIG. 3.

FIG. 9A is a view of the left end of FIG. 9.

FIG. 10 is a section view of FIG. 9A taken at section line 10-10 of FIG. 9.

FIG. 11 is an elevation view of the collection module of FIGS. 8-10.

FIG. 17 is taken at section line 17-17 of FIG. 16 and FIG. 18 is taken at section line 18-18 of FIG. 16.

DESCRIPTION OF THE PREFERRED EMBODIMENT

Figure 1:
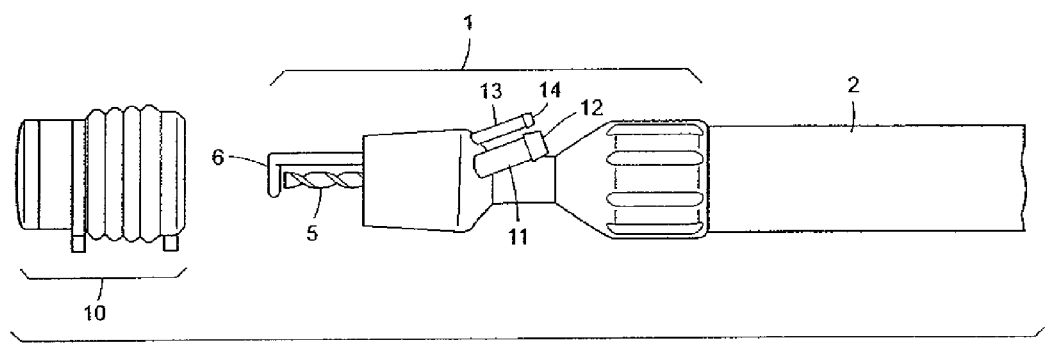
FIG. 1 is an expanded perspective view of a bone cutting tool (a craniotome) of the invention which has been provided with integral irrigation and suction systems. A collection module of the invention is illustrated to the left before attachment to the tool. The craniotome is attached to a handpiece which in turn is attached to a pneumatic line or an electric power source.

FIG. 1 is an expanded perspective view of a bone cutting tool of the invention having integral irrigation and suction systems. The tool is a craniotome which is used to cut an opening in the skull for brain surgery. The craniotome 1 is attached to a handpiece 2 which in turn is attached to a pneumatic line 3 (see FIGS. 2-4) or an electric power source. Cutting burr 5 has a diameter and an axis and is actuated by a foot switch (not shown). And the foot plate 6 is used to guide the tool along the inside of the skull in order to prevent penetration of the dura. A suction tube 11 is provided with a barbed fitting 12 and an irrigation tube 13 has a barbed fitting 14. Collection module 10 is illustrated before it is attached to craniotome 1.

FIG. 2 is a perspective view of FIG. 1 with the collection module 10 of the invention attached to the craniotome. A flexible bellows 15 is shown in this embodiment with a cylindrical duct in the form of shield 16 and a cap in the form of elastomeric seal 17 affixed at the distal end of the shield, the proximal end of the shield being affixed to the distal end of the bellows. The shield 16 has a diameter and is approximately coaxial with the axis of the cutting burr 5. The shield normally will be comprised of a relatively stiff, clear plastic tube.

Figure 4:
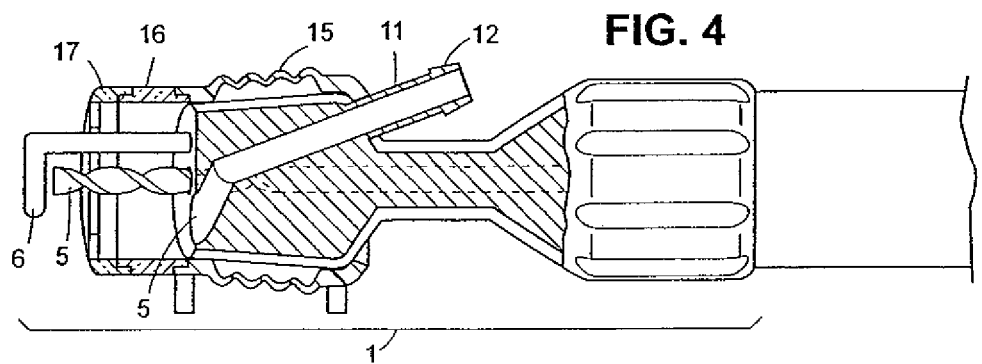
FIG. 4 is a section view of FIG. 3A taken at section line 4-4 of FIG. 3A and illustrating a portion of the suction system.

FIG. 3 is an elevation view of FIG. 2 and FIG. 4 is a section view of FIG. 3.

Figure 4A:
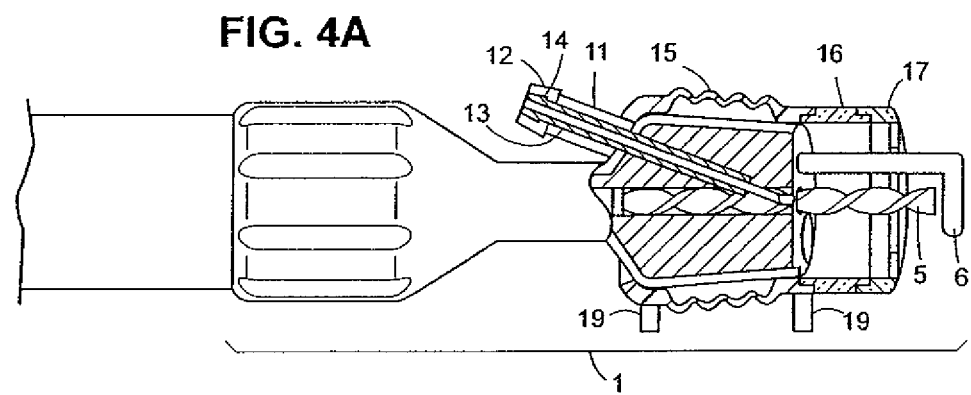
FIG. 4A is a section of FIG. 3A taken at section line 3-3 of FIG. 3A and illustrating a portion of the irrigation system.

FIG. 4 illustrates suction tube 11 which has an open mouth 23 at its distal end around cutting burr 5. FIG. 4A is a different section view of FIG. 3 which illustrates irrigation tube 13 of the irrigation system.

Figure 5:
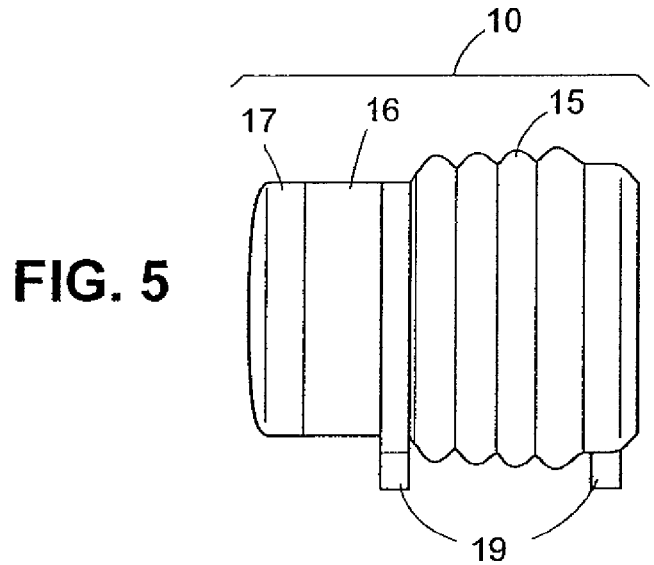
FIG. 5 is an elevation view of a collection module of the invention.
Figure 6:
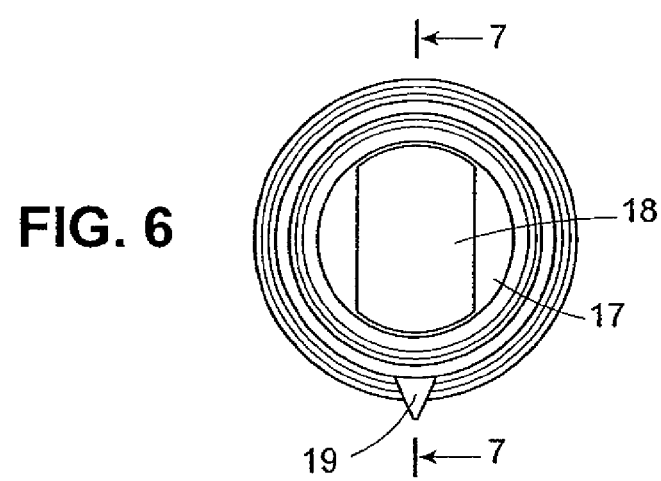
FIG. 6 is a distal end view of the collection module of FIG. 5.
Figure 7:
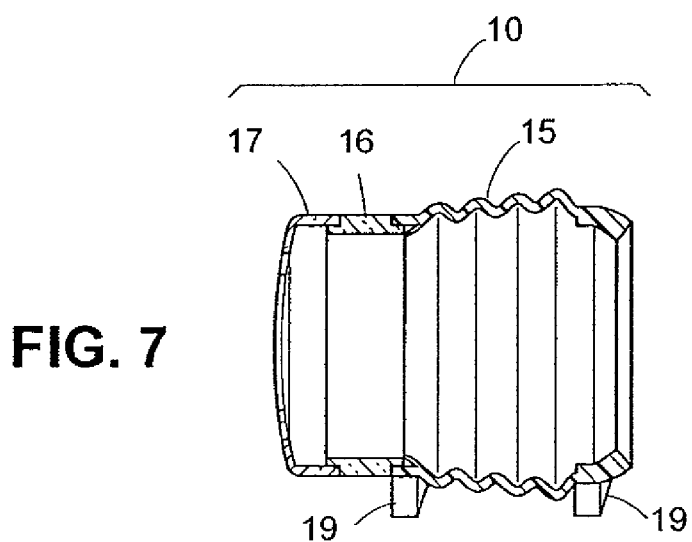
FIG. 7 is a section view of the collection module of FIGS. 5 and 6.

FIG. 5 illustrates the collection module 10 in an elevation view and FIG. 6 illustrates the distal end of the collection module 10. FIG. 7 is a section view of the collection module 10.

Figure 8:
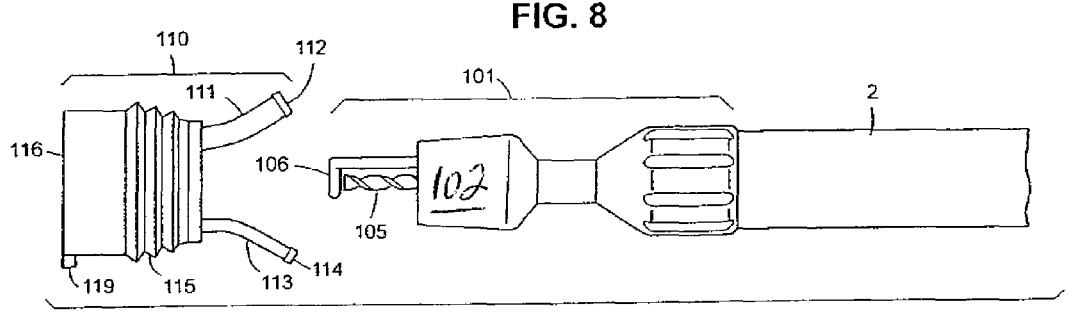
FIG. 8 is an expanded elevation view of a standard prior art craniotome and a collection module of the invention. This embodiment of a collection module is for use with standard craniotomes and is illustrated to the left before attachment to the tool.
Figure 9:
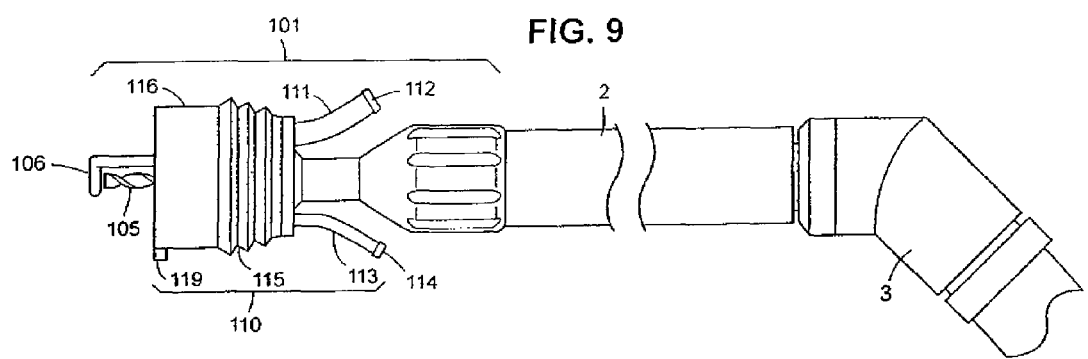
FIG. 9 is an elevation view of the craniotome of FIG. 8 with the collection module and the pneumatic line attached.
Figure 13:
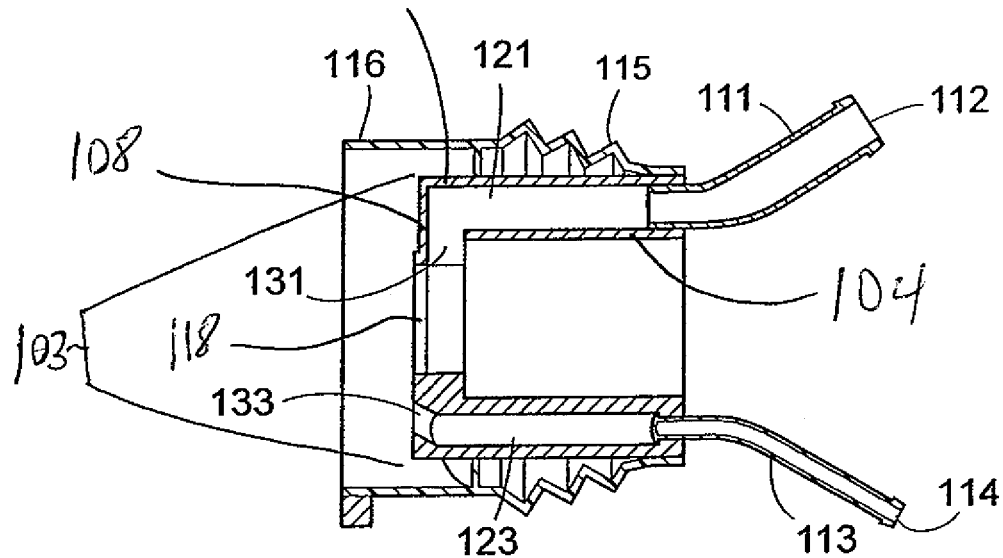
FIG. 13 is a section view of the collection module of FIGS. 11 and 12 taken at section line 13-13 of FIG. 12.

FIG. 8 illustrates in expanded elevation another embodiment of the invention. Collection module 110 is made for use with a standard prior art craniotome 101, the craniotome having a distal end 102. FIG. 9 is an elevation view of craniotome 101 with collection module 110 affixed thereto. The collection module 110 comprises a housing 103 (see also FIG. 13) having an inner wall 104, an outer wall 107 coaxially disposed around the inner wall and spaced therefrom, and an end wall 108 capping the distal end of the outer wall. The collection module 110 further comprises a suction tube 111 having a barbed fitting 112, an irrigation tube 113 having a barbed fitting 114, a flexible bellows 115 and a clear cylindrical tubular shield 116, the flexible bellows 115 and tubular shield 116 disposed around the housing 103 and extending distally beyond the distal end thereof. An optional indicator tab 119 is also illustrated. The craniotome has a foot plate 106 and a cutting burr 105.

FIG. 10 is a section view of FIG. 9 illustrating the relationship of the elements of collection module 110 to the craniotome 101. In particular, the suction tube 111 connects to a suction channel 121 and the irrigation tube 113 connects to an irrigation channel 123, the suction channel 121 and the irrigation channel 123 being disposed between the inner wall 104 and the outer wall 107.

Figure 12:
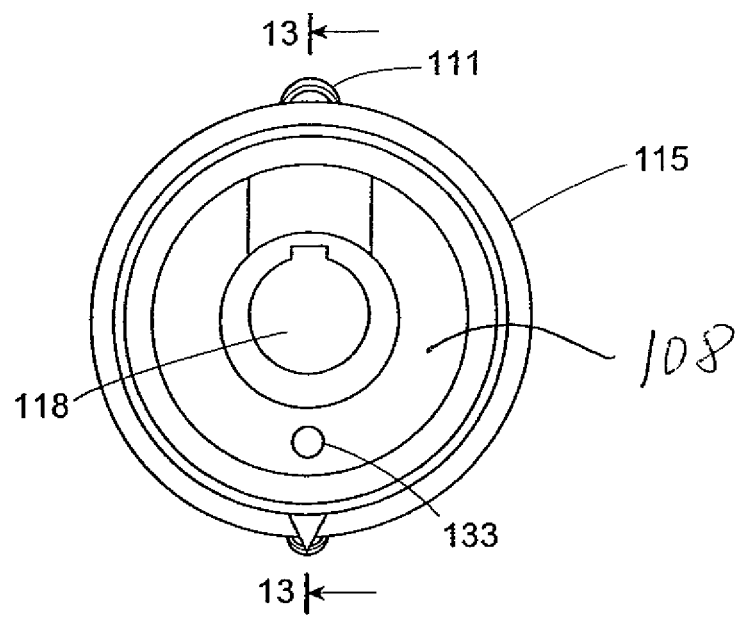
FIG. 12 is a distal end view of FIG. 11.

FIG. 11 is an elevation view of the collection module 110 by itself. The collection module 110 provides the irrigation and suction capability needed to carry out the objectives of the invention when a standard craniotome having no irrigation or suction capability is employed. (Some commercially available craniotomes have irrigation capability in which case the embodiment of FIG. 11 described herein can be made with suction capability but without irrigation capability as will be apparent to those skilled in the art.) This embodiment does not employ a seal of the type illustrated as element 17 in FIGS. 1-7. In FIG. 12, the distal end of the module is illustrated with a slot or opening 118 for a cutting burr and foot plate. An irrigation port 133 is also provided in end wall 108. Referring to the section view FIG. 13, the irrigation port 133 and the irrigation channel 123 are illustrated as well as the suction channel 121 and a suction port 131.

FIG. 8 illustrates in expanded elevation another embodiment of the invention. Collection module 110 is made for use with a standard prior art craniotome 101. FIG. 9 is an elevation view of craniotome 101 with collection module 110 affixed thereto. The collection module 110 comprises a suction tube 111 having a barbed fitting 112, an irrigation tube 113 having a barbed fitting 114, a flexible bellows 115 and a clear tubular shield 116. An optional indicator tab 119 is also illustrated. The craniotome has a foot plate 106 and a cutting burr 105.

The collection module 10 is adapted to the distal end of the craniotome 1 (as shown in FIGS. 2-4). Module 10 mates with the outer diameter of the craniotome 1 and is sealingly engaged therewith. The two are aligned in the correct orientation to set the slot 18 in the seal 17 in-line with the footplate 6. The burr 5 extends through slot 18 as illustrated in FIGS. 2 and 3. Slot 18 must be larger than burr 5, as illustrated, and the diameter of shield 16 must be larger than slot 18 as illustrated in FIGS. 3, 4, 4A, 6 and 7. Optional indicator tabs 19 (in the direction that the instrument will cut, arrow 20) can be used to facilitate correct orientation. The bellows 15 is constructed from an elastomer, allowing it to flex so that the distal portion of the collection module 10 can follow the irregularities of the skull 30 without excessive resistance. On the other end of the bellows is an internal lip seal 22 which prevents debris from being forced into the radial space between the craniotome 1 and the bellows 15. It should be noted that the cutting burr, or the drill bit or saw blade in other tools, may or may not extend beyond the distal end of the module when the tool is not in use. This is because the collection module is sufficiently flexible to allow such burr, bit or blade to extend beyond the distal end of the module when the tool is in use.

FIG. 10 is a section view of FIG. 9 illustrating the relationship of the elements of collection module 110 to the craniotome 101. In particular, the suction tube 111 connects to a suction channel 121 and the irrigation tube 113 connects to an irrigation channel 123.

Figure 15:
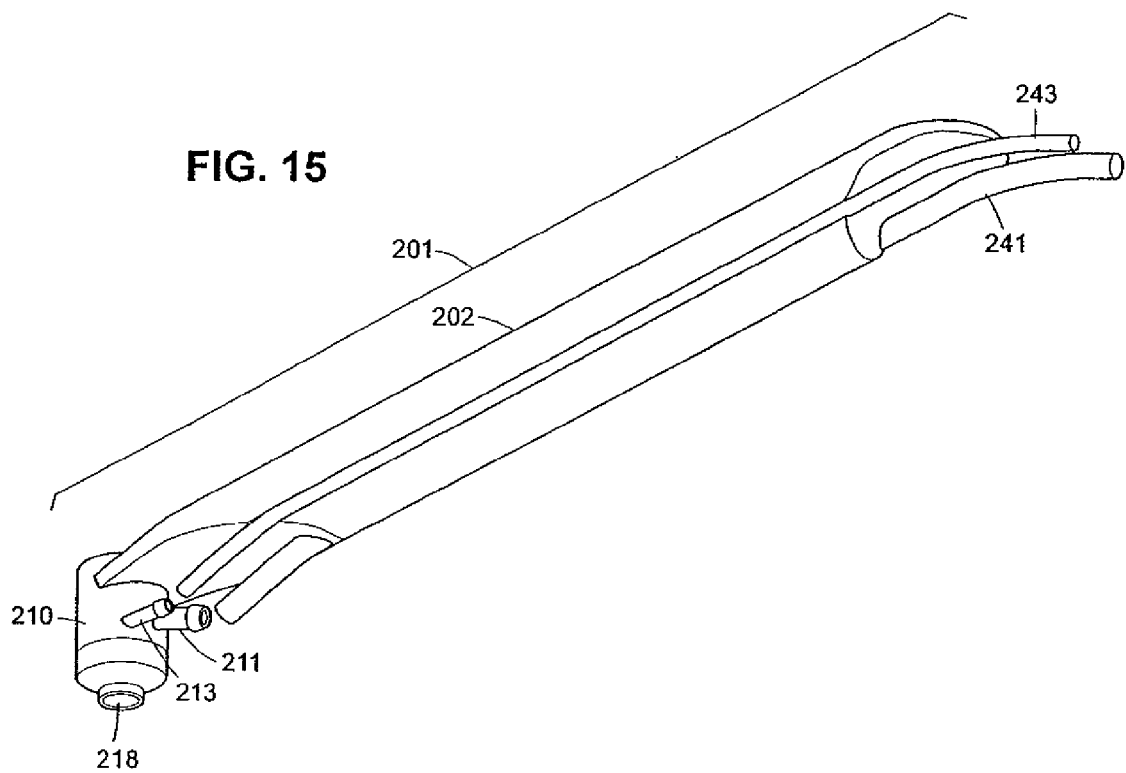
FIG. 15 is a perspective view of a drill guide of the invention which can suction and collect bone particulate during a bone drilling procedure.
Figure 16:
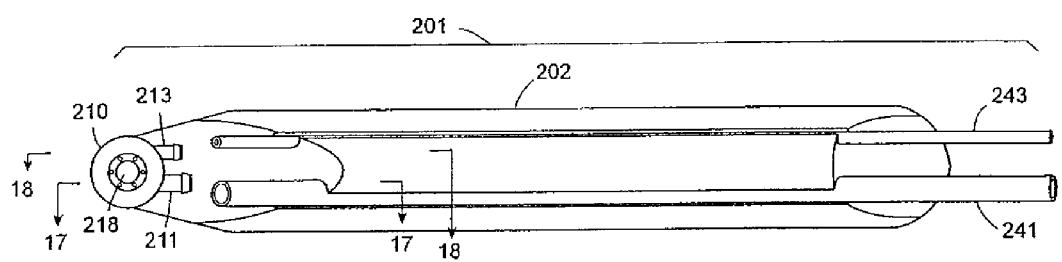
FIG. 16 is a bottom view of FIG. 15.

FIG. 15 is a perspective view of a drill guide of the invention which can suction and collect bone particulate in a sterile environment during a bone drilling procedure. The guide 201 comprises a handle 202 and a collection module 210. Sterile vacuum tube 241 connects to suction tube 211 and irrigant supply tube 243 connects to irrigation tube 213 during operation of the guide. Slot or opening 218 accommodates a drill bit 205 (see FIGS. 19 and 20) and irrigation and suctioning take place generally through the same opening. A bottom view of guide 201 is illustrated in FIG. 16.

FIG. 11 is an elevation view of the collection module 110 by itself. The collection module 110 provides the irrigation and suction capability needed to carry out the objectives of the invention when a standard craniotome having no irrigation or suction capability is employed. (Some commercially available craniotomes have irrigation capability in which case the embodiment of FIG. 11 described herein can be made with suction capability but without irrigation capability as will be apparent to those skilled in the art.) This embodiment does not employ a seal of the type illustrated as element 17 in FIGS. 1-7. In FIG. 12, the distal end of the module is illustrated with an opening 118 for a cutting burr and foot plate. An irrigation port 133 is also provided. Referring to the section view FIG. 13, the irrigation port 133 and the irrigation channel 123 are illustrated as well as the suction channel 121 and a suction port 131.

Figure 14:
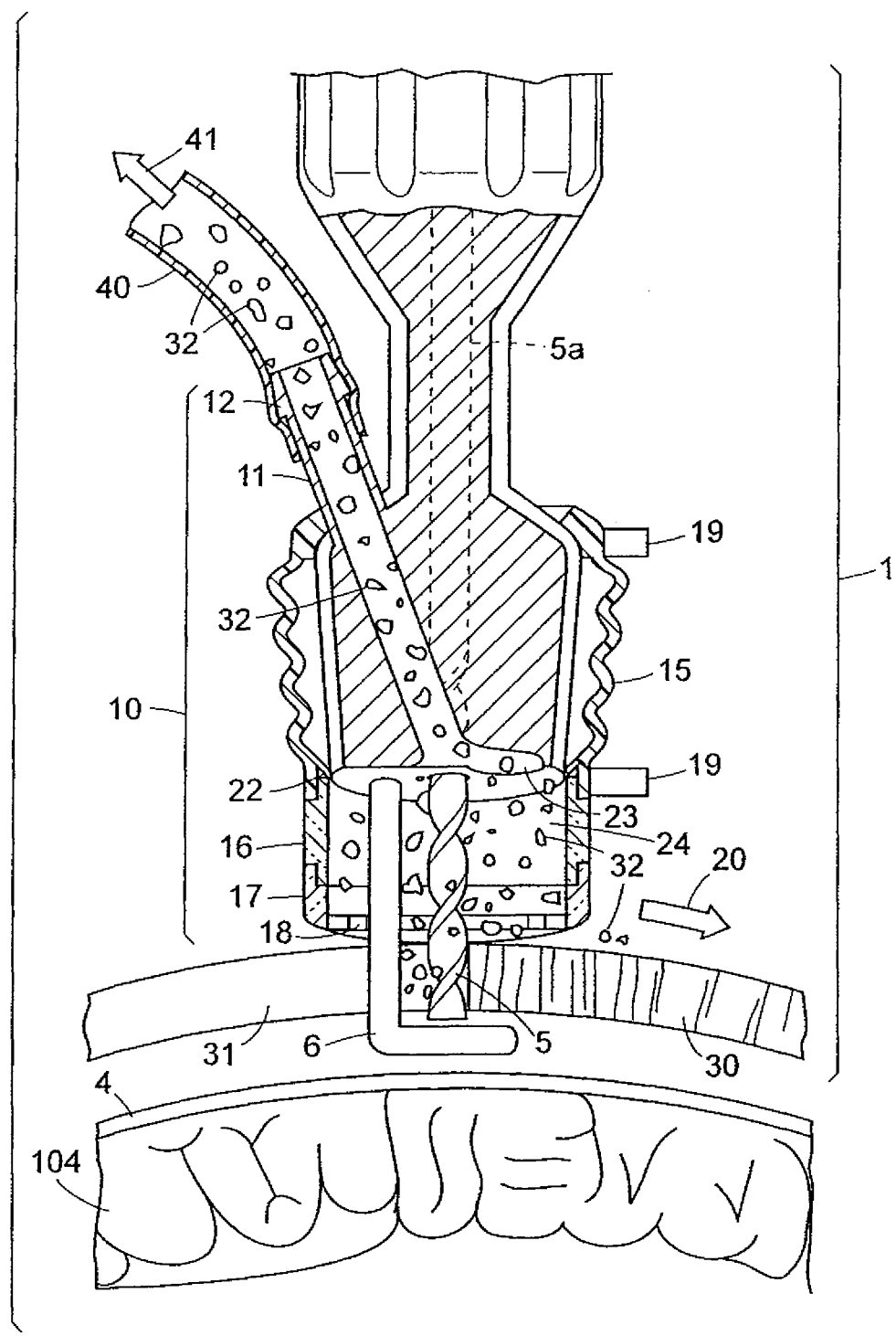
FIG. 14 is an illustration of an apparatus of the invention in operation during a cranial osteotomy.

FIG. 14 illustrates the operation of the distal (cutting) end of the embodiment of the invention illustrated in FIGS. 1-7. The craniotome 1 has a cutting burr 5 (and burr shaft 5a) and an integral foot plate 6. Unlike current instruments, however, the improved craniotome of the invention has many advantageous features. In this embodiment, the craniotome also incorporates internal passages for suction and irrigation. Each of these terminates proximally in a barbed fitting. The collection module 10 comprises an elastomeric bellows 15, a clear tubular shield 16 and an elastomeric seal 17. The collection module can constitute a preassembled, sterile, disposable item, although other configurations are certainly possible.

The collection module 10 is adapted to the distal end of the craniotome 1 (as shown in FIGS. 2-4). Module 10 mates with the outer diameter of the craniotome 1 and is sealingly engaged therewith. The two are aligned in the correct orientation to set the slot 18 in the seal 17 in-line with the footplate 6. Optional indicator tabs 19 (in the direction that the instrument will cut, arrow 20) can be used to facilitate correct orientation. The bellows 15 is constructed from an elastomer, allowing it to flex so that the distal portion of the collection module 10 can follow the irregularities of the skull 30 without excessive resistance. On the other end of the bellows is an internal lip seal 22 which prevents debris from being forced into the radial space between the craniotome 1 and the bellows 15. It should be noted that the cutting burr, or the drill bit or saw blade in other tools, may or may not extend beyond the distal end of the module when the tool is not in use. This is because the collection module is sufficiently flexible to allow such burr, bit or blade to extend beyond the distal end of the module when the tool is in use.

The shield 16 is a relatively stiff, clear tubular section that forms the radial wall of the collection module 10. Attached to the distal end of the shield 16 is the elastomeric seal 17. Ideally this would be a relatively clear material as well to aid in visualizing the cut. The seal 17 has an optionally, outwardly domed flexible end with a slot 18 to better contain and suction the bone particulate. The domed shape limits the contact area with the bone to reduce resistance. As the surgeon operates the craniotome, he applies both sideways force to cut as well as upward force to keep the tip of the footplate 6 in contact with the underside of the skull. This allows the footplate to ride between the dura 4 (the outer covering of the brain 104) and the inner table of the skull 30. Ahead of the cutting burr 5 is solid skull 30 and trailing the cutting burr is the kerf 31. The rotation of the cutting burr 5 and its helical flutes help to draw much of the bone particulate 32 upwards into a collection chamber 24 of the collection module. A funnel shaped depression or mouth 23 at the junction of the suction tube 11 and the distal face of the craniotome guides these bone fragments into the suction tube 11 and draws in by vacuum additional bone particles, irrigant and bodily fluids. The suction tube 11 is connected to a sterile vacuum tube 40. A barbed fitting 12 is provided for this connection. The sterile vacuum tube 40 is connected downstream to a containment module 60 as will be discussed later. (See FIG. 26.) Suction is applied to tube 40 and the result is that all material aspirated into the collection module 10 (bone fragments, irrigant, blood, tissue, etc.) is evacuated in the direction of arrow 41. The irrigation system is not illustrated because it is behind the suction system in this drawing. But the irrigation system is illustrated and discussed above in connection with FIGS. 1, 2 and 4A. Irrigant supply can be most easily provided from a pressurized IV bag of saline or from a hand syringe, peristaltic pump, sterile compressed gas source, or other common means. When the irrigant is a combination of gas and liquid an additional channel can be provided in either the craniotome of the invention (see FIGS. 1-4 and 14) or the collection module, for the purpose of introducing a second irrigation means. This additional channel could communicate with the liquid channel to serve as a mixing device as will be apparent to those having skill in the art based on the disclosures herein.

Figure 23:
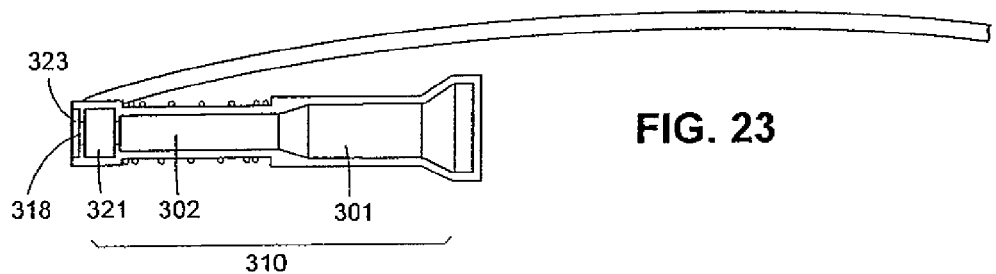
FIG. 23 is a section view of FIG. 22 taken at section line 23-23 of FIG. 22.

FIG. 23 is a section view of collection module 310 illustrating a collection chamber 321 and irrigation duct 323 in relation to slot or opening 318.

FIG. 15 is a perspective view of a drill guide of the invention which can suction and collect bone particulate in a sterile environment during a bone drilling procedure. The guide 201 comprises a handle 202 and a collection module 210. Sterile vacuum tube 241 connects to suction tube 211 and irrigant supply tube 243 connects to irrigation tube 213 during operation of the guide. Opening 218 accommodates a drill bit 205 (see FIGS. 19 and 20) and irrigation and suctioning take place generally through the same opening. A bottom view of guide 201 is illustrated in FIG. 16.

Figure 17:
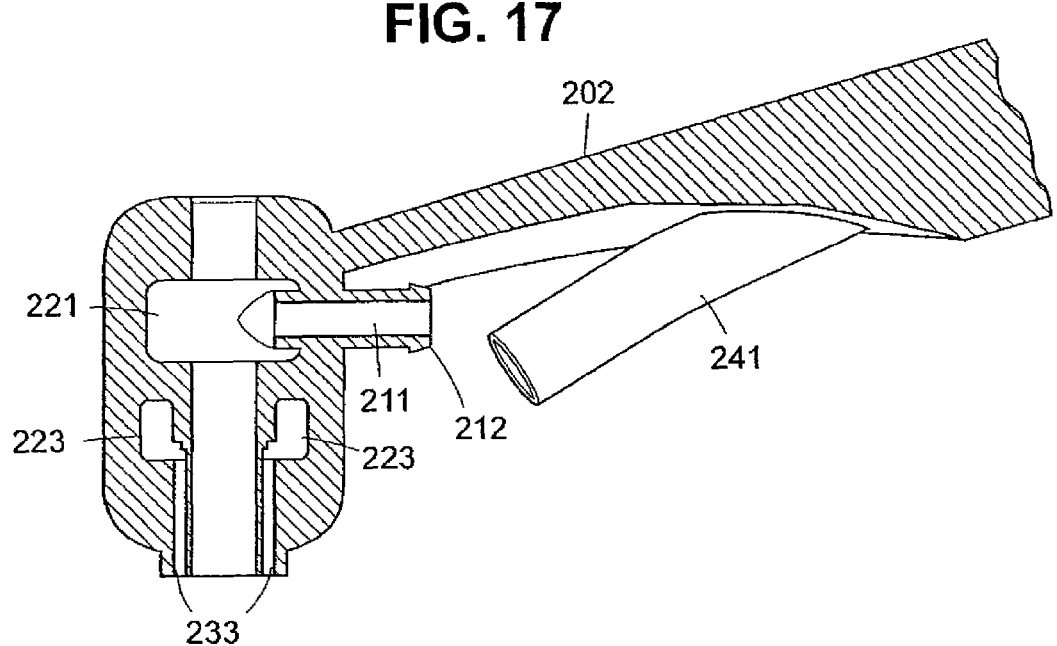
FIGS. 17 and 18 are partial section views of FIG. 16.
Figure 18:
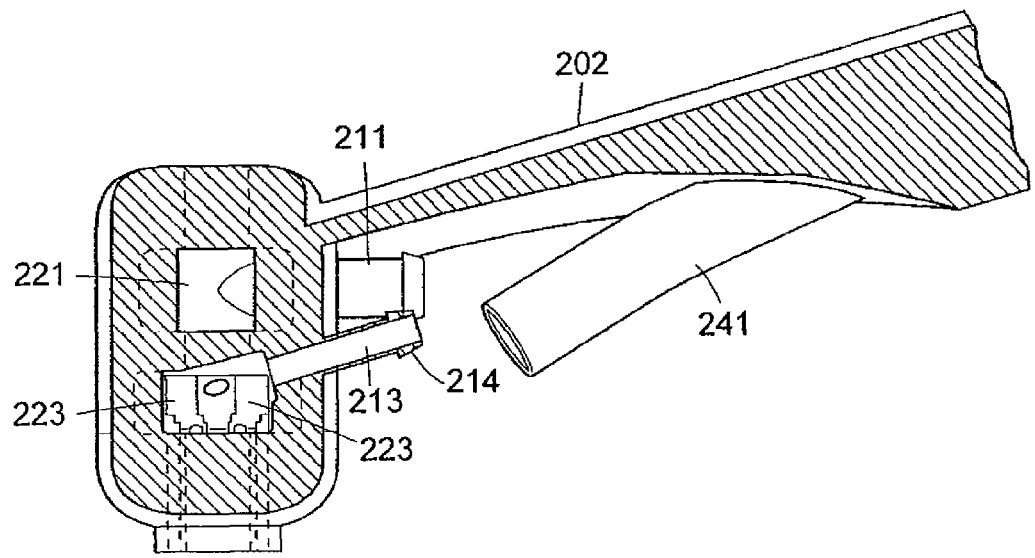

FIGS. 17 and 18 are section views of collection module 210 taken through line A-A and line B-B, respectively, of FIG. 16. The FIG. 17 section illustrates a barbed fitting 212 at the end of suction tube 211 and the connection of tube 211 with suction chamber 221. Irrigation channel 223 and irrigation ports 233 are illustrated. The FIG. 18 section illustrates another part of suction chamber 221. The FIG. 18 section also illustrates the barbed fitting 214 at the end of irrigation tube 213 and the connection of tube 213 with irrigation channel 223.

Figure 19:
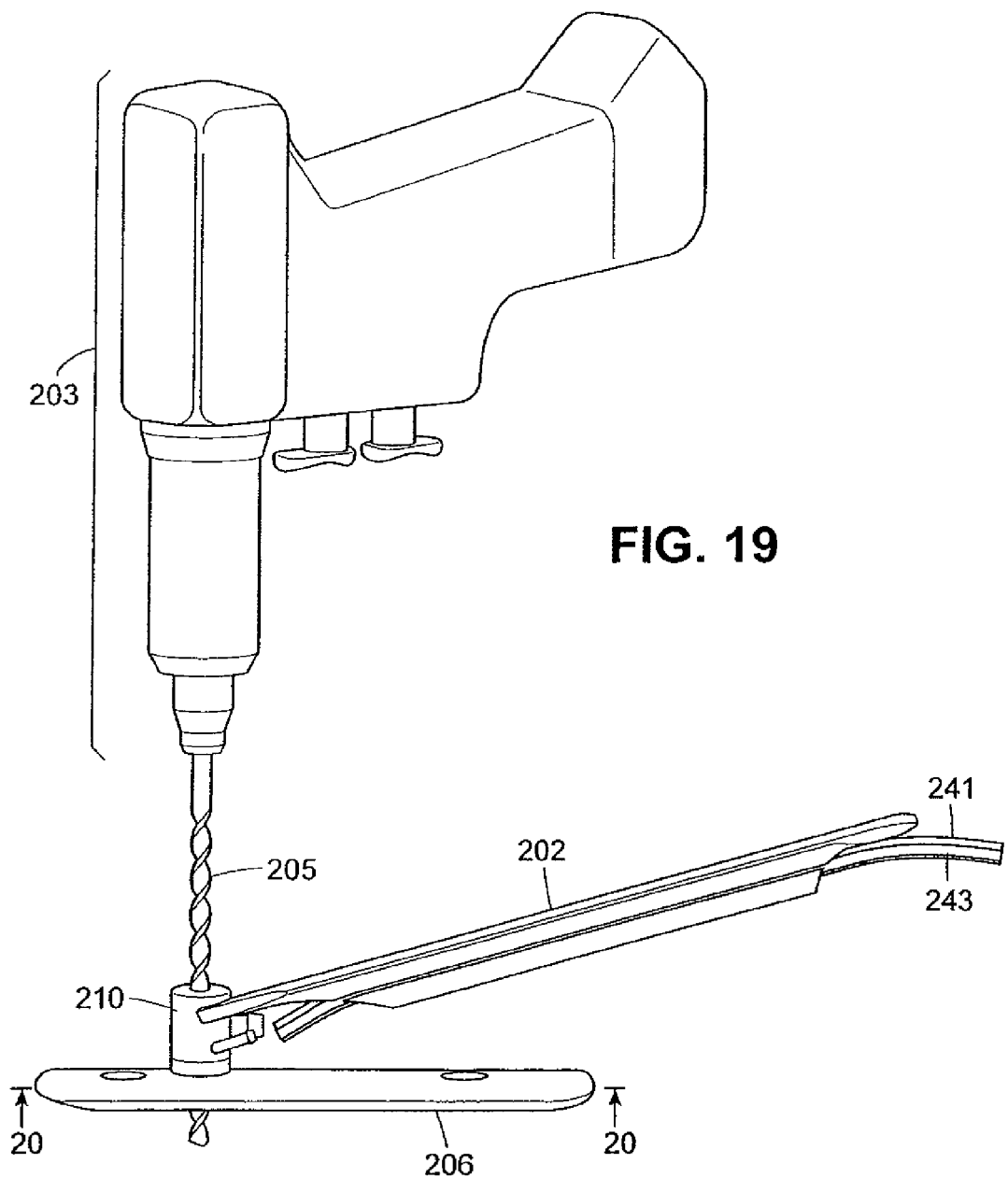
FIG. 19 is a perspective view of the guide of FIG. 15 illustrating the relationship of the guide to a drill and a bone plate.
Figure 20:
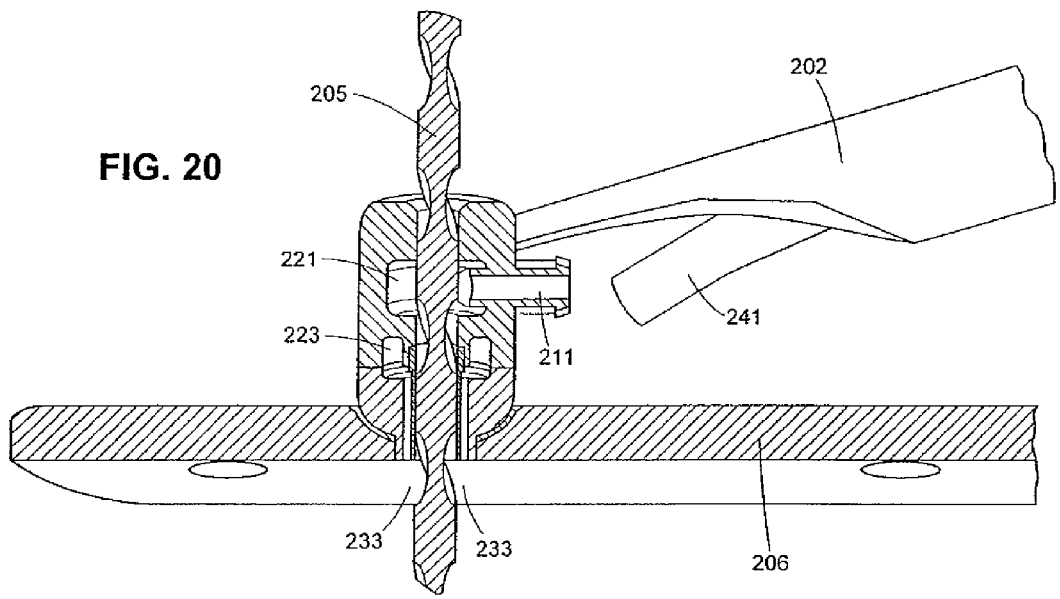
FIG. 20 is a partial section of FIG. 19 taken at section line 20-20 of FIG. 19.

A perspective view illustrating the relationship of the guide with a drill 203, drill bit 205 and a bone plate 206 is illustrated in FIG. 19. FIG. 20 is a partial section of FIG. 19 illustrating the relationship of drill bit 205 to the suction chamber 221, irrigation channel 223 and irrigation ports 233. During drilling, bone particulate is carried upward by the drill bit 205 and by suction. Suction vacuum tube 241 is connected to suction tube 211 and the particulate bone is carried by vacuum to a sterile containment module 60 (see FIG. 26). The operating area is irrigated by irrigant exiting irrigation ports 233.

Figure 21:
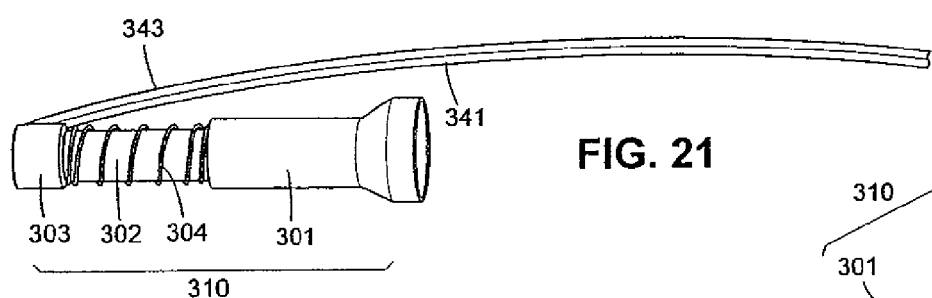
FIG. 21 is a perspective view of another embodiment of a bone particulate collection system for use with a drill.

FIG. 21 is a perspective view of another embodiment of a bone particulate collection system for use with a drill. Collection module 310 is comprised of an outer telescoping section 301 and an inner telescoping section 302. A spring 304 is biased between section 301 and distal end section 303. When drilling, inner telescoping section 302 telescopes into outer telescoping section 301 and when the drilling is complete spring 304 returns section 302 to its original position (as illustrated). Sterile vacuum tube 341 and irrigant supply tube 343 are also illustrated.

Figure 22:
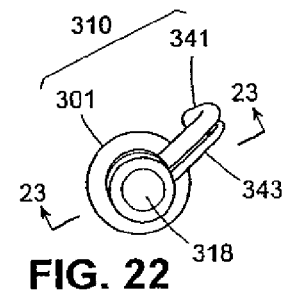
FIG. 22 is a distal end view of FIG. 21.

FIG. 22 is a distal end view of the collection module 310 also illustrating opening 318 which accommodates a drill bit 305 (see FIGS. 24 and 25) and irrigation and suctioning take place through the same opening.

FIG. 23 is a section view of collection module 310 illustrating a collection chamber 321 and irrigation duct 323 in relation to opening 318.

Figure 24:
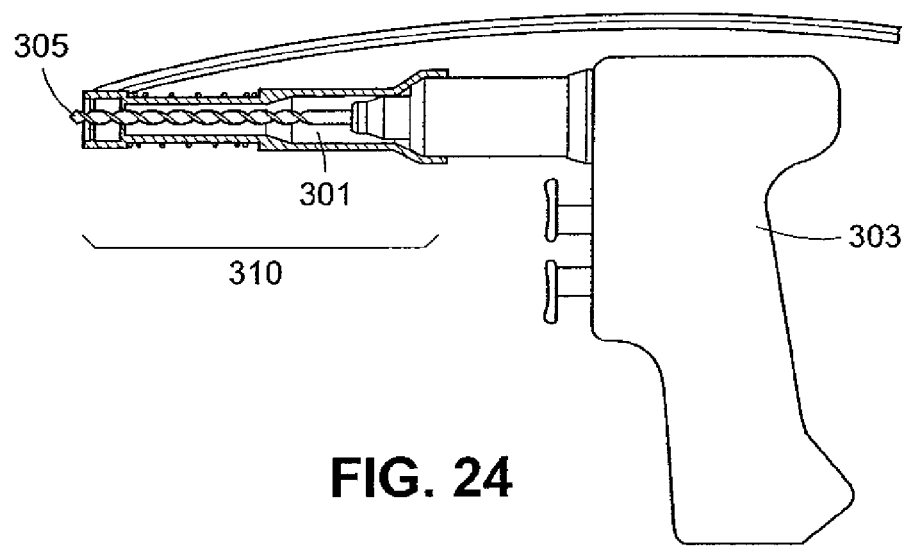
FIG. 24 is an elevation view of a transparent embodiment of the FIG. 21 collection module affixed to a drill.
Figure 25:
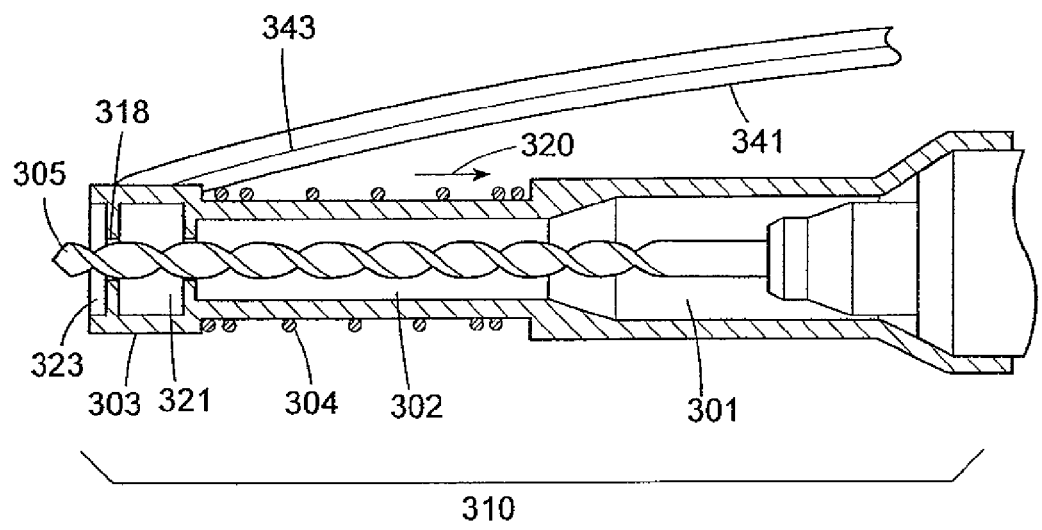
FIG. 25 is an enlarged section view of a portion of FIG. 24.

FIG. 24 is an elevation view of a transparent embodiment of collection module 310 affixed to drill 303 having a drill bit 305. An enlarged section view of a portion of FIG. 24 is provided in FIG. 25. Arrow 320 illustrates the direction of the telescoping movement of section 302 into section 301 when the drill bit is drilled into a bone. Spring 304 causes section 302 to return to the position illustrated when drilling is completed. Sterile vacuum tube 341 is in suctioning communication with suction chamber 321 and irrigant supply tube 343 is in irrigating communication with irrigation duct 323. The suctioning and irrigating operations function in the same manner as the other embodiments of the invention discussed above.

FIGS. 1-25 depict just a few possible configurations of a cutting or drilling and collection apparatus of the invention which would be consistent with the method of the invention. The principles of the invention can easily be adapted to other osteotomy instruments (e.g. an oscillating saw, a rotary saw or a reciprocating saw) to achieve the same results.

According to the method of the invention, a surgeon can simultaneously cut or drill bone and irrigate and suction with essentially no additional effort. Eliminated is the splatter of the irrigant and cutting debris and also the need for an assistant to precisely coordinate with the movements of the surgeon as he or she irrigates and suctions. These benefits however, are secondary to the main purpose of the apparatus and method of the invention, namely, the ability to collect the sterile bone particulate generated by the osteotomy or drilling process for use in the reconstructive portion of the procedure.

Figure 26:
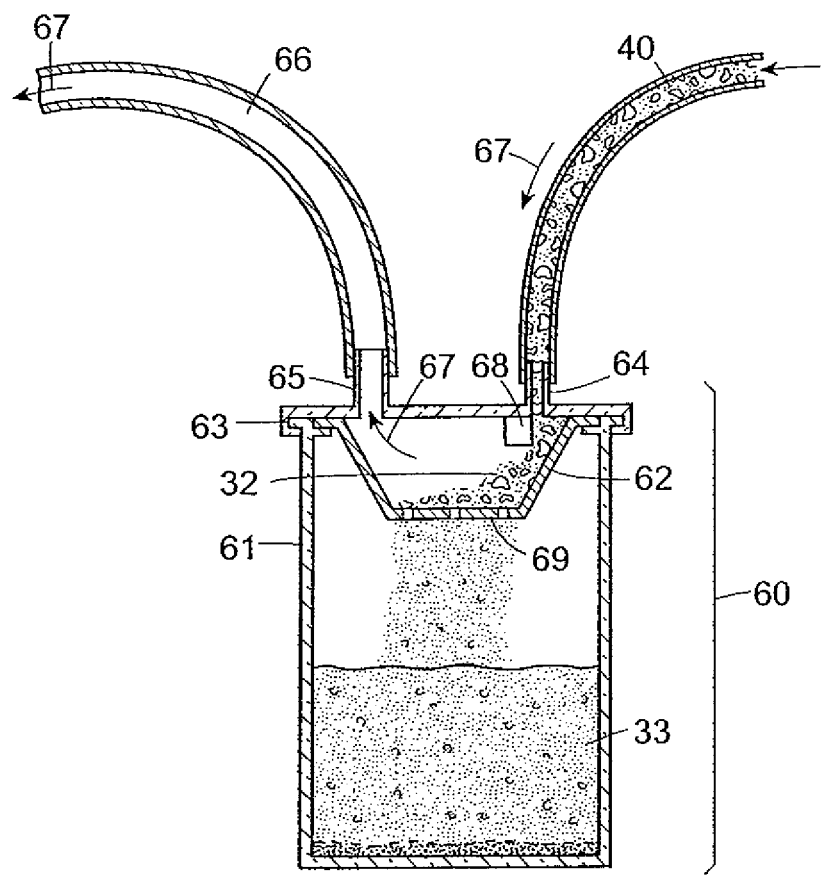
FIG. 26 illustrates a sterile containment module of the invention.

FIG. 26 illustrates an embodiment of a sterile containment module 60 for the separation of the bone particles 32 from liquids 33, the liquids comprising irrigant and body fluids. Unlike traditional hospital suction systems, this is a sterile system so that the bone particles collected can be reused in the reconstructive portion of surgery.

The aspirate from the containment chamber is conveyed though the sterile vacuum tube 40 to the containment module 60. The aspirate consists of bone particles, irrigant, small amounts of tissue, blood and other body fluids. The containment module comprises three sterile parts: the canister 61, the collection cup 62 and the cover 63. Of course, other embodiments are certainly possible and would be apparent to those skilled in the art based upon the disclosures herein. It is envisioned that all three items would be provided as a sterile unit for single use. All could be produced (molded) from a clear polymer for visualizing the contents. The suction tube 40 connects to a fitting 64 molded into the cover. A second fitting 65 is then connected to the hospital suction system in a sterile fashion through tube 66. The suction travels in the direction of the arrows 67. When the aspirate enters the canister 61, a deflector 68 forces the flow downward and gravity then separates the contents (solid and liquid) from the air flow. The solids and liquids fall into the cup 62 and settle to the bottom where perforations 69 allow the liquid to drain into the bottom of the canister 61. Optionally the cup may be fitted with a filter to better trap the smaller bone particles. At the conclusion of the osteotomy or drilling procedure, the bone particles in the cup can be left to drain until needed, at which point the cover 63 is removed and the cup 62 is extracted with its sterile contents. As mentioned previously, the bone particles can then be used "as is" or mixed with other biological additives for use in the reconstructive portion of the procedure.

In today's operating room environment, the contents of the canister 61 described above are simply suctioned into the non-sterile hospital system and discarded. A valuable and much-needed commodity, (autologous) bone graft, is simply wasted and later replaced with autograft harvested from a second site, allograft or with alloplastic materials.

What is claimed is:

1. An apparatus for collecting particulate bone during a craniotomy, comprising:
    a craniotome tool having a tool body with a distal end, a bone cutting or drilling bun and a foot plate extending out from the distal end of the tool body, the foot plate extending beyond the bone cutting or drilling burr and the bone cutting or drilling bun having a diameter;
    a collection module adapted for removable engagement with the distal end of the tool body of the craniotime tool, the collection module having a housing comprising:
        a cavity accommodating therein the distal end of the tool body, a proximal end of the housing having a flexible bellow portion, and a distal end of the flexible bellow portion having a protruding lip adapted to seal a radial space in the cavity between the flexible bellow portion and the distal end of the tool body accommodated therein, the protruding lip extending from and forming part of an inner wall of the flexible bellow portion to prevent debris from entering the radial space;

a transparent shield portion extending from the distal end of the flexible bellow portion;

an end wall forming part of a dome-shaped end portion extending from a distal end of the transparent shield portion, the end wall having a slot sufficiently larger than the diameter of the bone cutting or drilling burr to permit the bone cutting or drilling burr to extend therethrough; and a suction channel disposed in the cavity in suctioning communication with the slot.

2. The apparatus of claim 1 further comprising an irrigation channel disposed in the cavity and in irrigating communication with the slot.

3. The apparatus of claim 2 further comprising an irrigation tube connected to the irrigation channel.

4. The apparatus of claim 1 further comprising a containment module connected to a distal end of the suction channel.

5. The apparatus of claim 1 wherein the collection module is disposable.

6. The apparatus of claim 1 further comprising a suction tube connected to the suction channel.

* * * * *